(12) United States Patent
Keil et al.

(10) Patent No.: US 11,745,023 B2
(45) Date of Patent: *Sep. 5, 2023

(54) HIGH VOLTAGE THERAPY SYSTEM WITH LOW SIDE CONTROL

(71) Applicant: CARDIAC PACEMAKERS, INC., St. Paul, MN (US)

(72) Inventors: Brandon Tyler Keil, Maple Grove, MN (US); Paul John McNamee, Roseville, MN (US); William J. Linder, Golden Valley, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 172 days.

This patent is subject to a terminal disclaimer.

(21) Appl. No.: 17/199,716

(22) Filed: Mar. 12, 2021

(65) Prior Publication Data

US 2021/0283409 A1    Sep. 16, 2021

Related U.S. Application Data

(60) Provisional application No. 62/988,497, filed on Mar. 12, 2020.

(51) Int. Cl.
*A61N 1/39* (2006.01)
*A61N 1/378* (2006.01)

(52) U.S. Cl.
CPC ........... *A61N 1/3956* (2013.01); *A61N 1/378* (2013.01); *A61N 1/3912* (2013.01)

(58) Field of Classification Search
CPC ..... A61N 1/3956; A61N 1/378; A61N 1/3912
See application file for complete search history.

(56) References Cited

U.S. PATENT DOCUMENTS

| | | | |
|---|---|---|---|
| 5,507,781 A | 4/1996 | Kroll et al. | |
| 5,643,323 A | 7/1997 | Kroll et al. | |
| 6,331,794 B1 * | 12/2001 | Blanchard | H03K 17/6871 327/112 |
| 6,647,292 B1 | 11/2003 | Bardy et al. | |
| 6,721,597 B1 | 4/2004 | Bardy et al. | |
| 6,754,528 B2 | 6/2004 | Bardy et al. | |
| 6,778,860 B2 | 8/2004 | Ostroff et al. | |
| 6,865,417 B2 | 3/2005 | Rissmann et al. | |
| 6,952,608 B2 | 10/2005 | Ostroff | |
| 6,954,670 B2 | 10/2005 | Ostroff | |
| 6,968,231 B1 | 11/2005 | Silvian et al. | |
| 7,149,575 B2 | 12/2006 | Ostroff et al. | |
| 7,330,757 B2 | 2/2008 | Ostroff et al. | |

(Continued)

*Primary Examiner* — Eric D. Bertram
(74) *Attorney, Agent, or Firm* — Seager, Tufte & Wickhem LLP

(57) ABSTRACT

Improved devices, circuits and methods of operation in implantable stimulus systems. An implantable defibrillator may comprise a charging circuit using a transformer to store and build up energy on an HV capacitor or capacitor stack, with the HV capacitor in turn coupled to an H-bridge output circuit having low and high sides for issuing therapy. In the output current path, a current controlling circuitry is placed between the H-bridge and ground, allowing the greater flexibility in the selection of switching devices, and drivers for such devices, in the H-bridge circuit and/or enabling circuits between the H-bridge and the HV capacitor or other therapy circuit.

17 Claims, 6 Drawing Sheets

(56) References Cited

U.S. PATENT DOCUMENTS

| | | |
|---|---|---|
| 7,555,338 B2 | 6/2009 | Ostroff |
| 7,783,340 B2 | 8/2010 | Sanghera et al. |
| 7,860,565 B2 | 12/2010 | Brink |
| 7,877,139 B2 | 1/2011 | Ostroff |
| 8,157,813 B2 | 4/2012 | Ko et al. |
| 8,160,686 B2 | 4/2012 | Allavatam et al. |
| 8,200,341 B2 | 6/2012 | Sanghera et al. |
| 8,209,005 B1 * | 6/2012 | Moulder ............... A61N 1/3925 607/17 |
| 8,463,392 B2 | 6/2013 | Aghassian |
| 8,473,066 B2 | 6/2013 | Aghassian et al. |
| 8,532,785 B1 | 9/2013 | Crutchfield et al. |
| 8,548,590 B2 | 10/2013 | Aghassian |
| 8,565,878 B2 | 10/2013 | Allavatam et al. |
| 8,825,157 B2 | 9/2014 | Warren et al. |
| 8,972,005 B2 | 3/2015 | Rasmussen et al. |
| 8,983,599 B2 | 3/2015 | Garrett et al. |
| 9,283,398 B2 * | 3/2016 | Ostroff ............... A61N 1/39622 |
| 9,579,517 B2 | 2/2017 | Meador et al. |
| 9,641,012 B2 | 5/2017 | Cabelka et al. |
| 9,643,025 B2 | 5/2017 | Crutchfield et al. |
| 9,750,950 B2 | 9/2017 | Norton et al. |
| 9,814,889 B2 | 11/2017 | Strommer et al. |
| 9,861,827 B2 | 1/2018 | Cabelka et al. |
| 9,861,828 B2 | 1/2018 | Norton et al. |
| 9,956,442 B2 | 5/2018 | Cooper et al. |
| 10,046,168 B2 | 8/2018 | Nikolski et al. |
| 10,050,700 B2 | 8/2018 | Ludwig et al. |
| 10,080,905 B2 | 9/2018 | Anderson et al. |
| 10,155,119 B2 | 12/2018 | Anderson et al. |
| 10,159,847 B2 | 12/2018 | Rasmussen et al. |
| 10,213,610 B2 | 2/2019 | Maile et al. |
| 10,350,425 B2 | 7/2019 | Nikolski et al. |
| 10,471,267 B2 | 11/2019 | Thompson-Nauman et al. |
| 10,556,118 B2 | 2/2020 | Anderson et al. |
| 2006/0167503 A1 | 7/2006 | Warren et al. |
| 2006/0241698 A1 * | 10/2006 | Ostroff ................ A61N 1/3937 607/2 |
| 2008/0077189 A1 * | 3/2008 | Ostroff ................ A61N 1/3956 607/27 |
| 2010/0280577 A1 * | 11/2010 | Roy ....................... A61N 1/378 323/280 |
| 2012/0029335 A1 | 2/2012 | Sudam et al. |
| 2012/0197325 A1 * | 8/2012 | Sauer ................... A61N 1/3981 607/5 |
| 2014/0343625 A1 * | 11/2014 | O Laighin ......... A61N 1/36034 607/48 |
| 2016/0166841 A1 * | 6/2016 | Ostroff ................ A61N 1/3912 607/4 |
| 2017/0021159 A1 | 1/2017 | Reddy et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2018/0036527 A1 | 2/2018 | Reddy et al. |
| 2018/0036547 A1 | 2/2018 | Reddy |
| 2018/0133462 A1 | 5/2018 | Reddy |
| 2021/0252296 A1 | 8/2021 | Keil et al. |
| 2021/0252299 A1 | 8/2021 | Keil |
| 2021/0257849 A1 | 8/2021 | Keil et al. |

* cited by examiner

HIGH VOLTAGE THERAPY SYSTEM WITH LOW SIDE CONTROL

CROSS REFERENCE TO RELATED APPLICATIONS

This application claims the benefit of and priority to U.S. Provisional Patent Application Ser. No. 62/988,497 filed on Mar. 12, 2020, the disclosure of which is incorporated herein by reference.

BACKGROUND

Battery powered implantable devices, such as implantable defibrillators, may generate output stimuli having a larger voltage than the batteries of such devices can directly provide. Voltage boosting circuitry is typically used to create the higher voltages, including, for example, switched capacitor and/or transformer-based DC:DC conversion circuitry. In an implantable defibrillator, for example, a DC:DC circuit, such as a flyback transformer circuit, can be used to transfer power from a battery to a high power capacitor stack until the energy stored on the capacitor stack meets a therapy threshold. The stored energy is then discharged to the patient.

When discharging energy to the patient, it is common to deliver therapy in a biphasic pattern that requires switching the direction of current flow. An H-Bridge circuit is often used to provide the switching capability. The switches of an H-Bridge, which may take the form of junction or field effect transistors, silicon controlled rectifiers, or other suitable circuitry, may be used in an ON/OFF manner, in which currents are not controlled, for delivering high power therapy such as defibrillation. It may be desirable in some instances to reuse this circuitry to provide controlled current outputs. New and alternative circuit designs and methods for providing controlled current outputs are desired.

OVERVIEW

The present inventors have recognized, among other things, that a problem to be solved is the need for new and/or alternative circuit designs for using and reusing defibrillation output circuitry to deliver controlled current pacing or induction pulses.

A first illustrative and non-limiting example takes the form of an electronic circuit for controlling an output of an implantable medical device, the electronic circuit comprising: an H-bridge comprising first and second high side legs having first and second high side switches, and first and second low side legs having first and second low side switches, defining first and second nodes for outputting a therapy signal from the implantable medical device; a first therapy output circuit coupled to the H-bridge; and a current controlling circuit coupled between the low side legs of the H-bridge and ground.

Additionally or alternatively, each of the first and second low side switches are latching devices.

Additionally or alternatively, each of the first and second high side switches are latching devices.

Additionally or alternatively, the coupling of the therapy output circuit to the H-bridge includes a first enable switch, the first enable switch being a latching device.

Additionally or alternatively, the circuit may further comprise a second therapy output circuit coupled by a second enable switch to the H-bridge, the second enable switch being a latching device.

Additionally or alternatively, the current controlling circuit comprises a current controlling switch coupled in series to a sense resistor, and a feedback circuit configured to receive a signal indicating a voltage drop across the sense resistor and generate a control signal to the current controlling switch.

Additionally or alternatively, the current controlling switch takes the form of an IGBT.

Additionally or alternatively, the current controlling switch takes the form of a high voltage MOSFET.

Additionally or alternatively, the current controlling switch takes the form of a high voltage bipolar junction transistor.

Additionally or alternatively, the circuit may further comprise a bypass path parallel to the current controlling circuit and configured to allow current to bypass the current controlling circuit.

Additionally or alternatively, the circuit may further comprise a bypass path parallel to the sense resistor and configured to allow a current from the current controlling circuit to bypass the sense resistor.

Additionally or alternatively, the bypass path may comprise a diode.

Additionally or alternatively, the bypass path may comprise a switch to selectively allow current to pass therethrough.

A second illustrative and non-limiting example takes the form of an implantable defibrillator comprising a housing and operational circuitry therein, the operational circuitry comprising: at least one battery; at least one high power capacitor; a transformer configured to selectively transfer energy from the battery to the high power capacitor; a system controller configured to control operation of the transformer, and an electronic circuit as in the first illustrative and non-limiting example or any of the above alternatives or additions thereto.

A third illustrative and non-limiting example takes the form of an implantable defibrillator comprising a housing and operational circuitry therein, the operational circuitry comprising: at least one battery; at least one high power capacitor; a transformer configured to selectively transfer energy from the battery to the high power capacitor; a system controller configured to control operation of the transformer; and an output control circuit coupled to the at least one high power capacitor, such that the at least one high power capacitor serves to provide power to a first therapy output circuit, and comprising: an H-bridge having first and second high side legs having first and second high side switches, and first and second low side legs with first and second low side switches, defining first and second nodes for outputting a therapy signal from the implantable medical device; and a current controlling circuit coupled between the low side legs of the H-bridge and ground.

Additionally or alternatively, the coupling of the first therapy output circuit to the H-bridge includes a first enable switch, the first enable switch being a latching device; each of the first and second low side switches, and each of the first and second high side switches, are latching switches; the current controlling circuit comprises a current controlling switch coupled in series to a sense resistor, and a feedback circuit configured to receive a signal indicating a voltage drop across the sense resistor and generate a control signal to the current controlling switch; and the current controlling switch is a non-latching switch enabling truncation of an output constant current signal.

A fourth illustrative and non-limiting example takes the form of a method of delivering an induction output and a defibrillation shock from a defibrillator, the defibrillator including: sensing circuitry for sensing whether a patient has a ventricular arrhythmia; an H-bridge comprising first and second high side legs having first and second high side switches, and first and second low side legs having first and second low side switches, defining first and second nodes for outputting a therapy signal from the implantable medical device; a current controlling circuit coupled between the low side legs of the H-bridge and ground; and a bypass path allowing at least a portion of the current controlling circuit to be bypassed; the method comprising: delivering the induction output by repeatedly performing the following for at least two cycles: first, enabling the first high side switch and second low side switch, thereby latching each in a closed state, while using the current controlling switch to control current through the H-bridge to deliver an induction pulse of a first polarity, and terminating the induction pulse of the first polarity by opening the current controlling switch, thereby de-latching the first high side switch and second low side switch; second, enabling the second high side switch and the first low side switch, thereby latching each in a closed state, while using the current controlling switch to control current through the H-bridge to deliver an induction pulse of a second polarity, and terminating the induction pulse of the second polarity by opening the current controlling switch, thereby de-latching the second high side switch and first low side switch; after delivering the induction output, determining, by using the sensing circuitry, that the patient has a ventricular arrhythmia, and delivering a defibrillation therapy using the H-bridge.

Additionally or alternatively, the bypass path may comprise a bypass switch positioned to bypass the entire current controlling circuit, the defibrillation therapy has first and second phases of opposite polarities from one another, and the step of delivering the defibrillation therapy using the H-bridge, comprises, in order: closing the bypass switch; enabling the first high side switch and second low side switch, thereby latching each in a closed state, to deliver the first phase of the defibrillation therapy in a first polarity; terminating the first phase by opening the bypass switch, thereby de-latching the first high side switch and second low side switch; again closing the bypass switch; enabling the second high side switch and the first low side switch, thereby latching each in a closed state, to deliver the second phase of the defibrillation therapy in a second polarity opposite the first polarity; and terminating the second phase by opening the bypass switch, thereby de-latching the second high side switch and first low side switch.

Additionally or alternatively, the current controlling circuit comprises a current controlling switch coupled in series to a sense resistor, and a feedback circuit configured to receive a signal indicating a voltage drop across the sense resistor and generate a control signal to the current controlling switch.

Additionally or alternatively, during delivery of the induction pulse of the first polarity and the induction pulse of the second polarity, the feedback circuit compares the signal indicating a voltage drop across the sense resistor to a current controlling reference voltage, to thereby provide a control signal to the current controlling switch.

Additionally or alternatively, the bypass path comprises a bypass switch positioned to bypass the sense resistor, the defibrillation therapy has first and second phases of opposite polarities from one another, and the step of delivering the defibrillation therapy using the H-bridge comprises, in order: closing the bypass switch and the current controlling switch; enabling the first high side switch and second low side switch, thereby latching each in a closed state, to deliver the first phase of the defibrillation therapy in a first polarity; terminating the first phase by opening at least one of the bypass switch and the current controlling switch, thereby de-latching the first high side switch and second low side switch; again closing the bypass switch and the current controlling switch; enabling the second high side switch and the first low side switch, thereby latching each in a closed state, to deliver the second phase of the defibrillation therapy in a second polarity opposite the first polarity; and terminating the second phase by opening at least one of the bypass switch and the current controlling switch, thereby de-latching the second high side switch and first low side switch.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
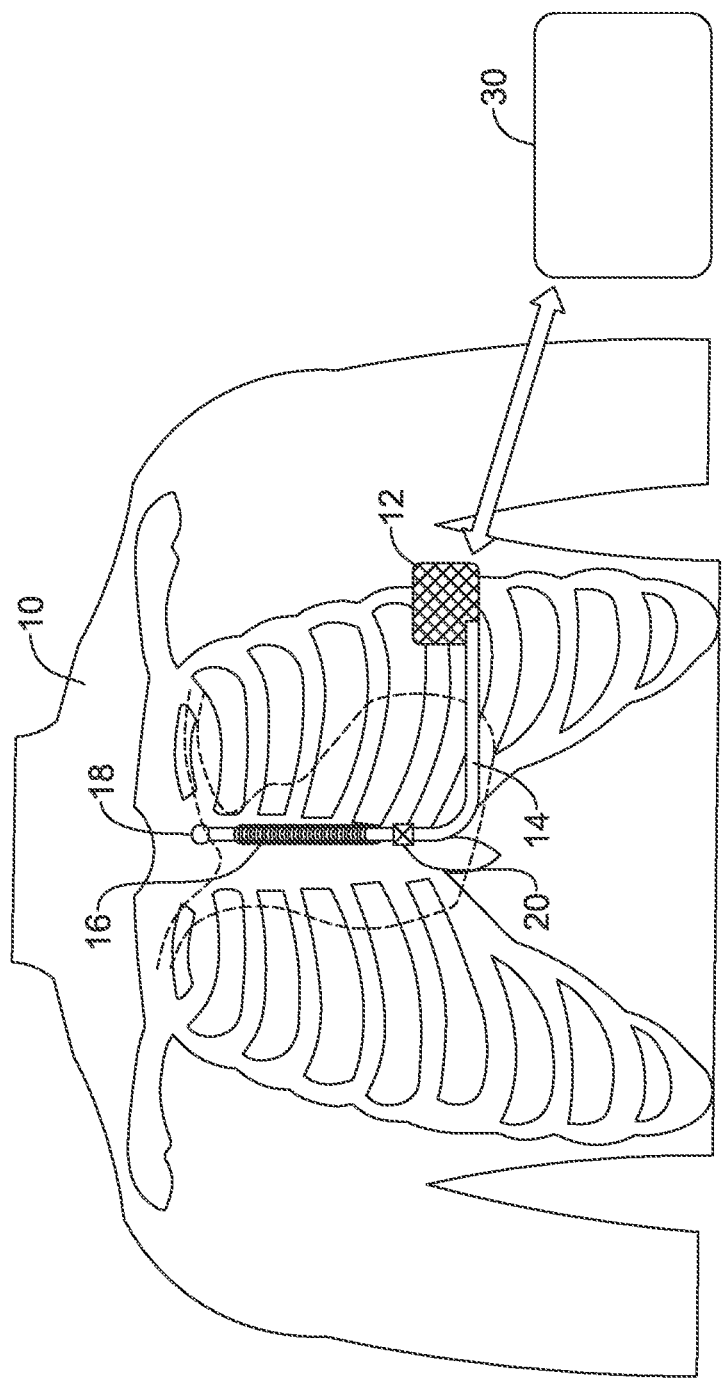
FIG. 1 shows an implantable stimulus system relative to the torso of a patient.

FIG. 1 shows an implantable stimulus system relative to the torso of a patient 10. In the example shown, an implantable canister 12 is placed near the left axilla, with a lead 14 extending medially therefrom. The lead 14 turns near the xiphoid to advance in a superior direction, toward the head generally parallel the sternum and over the heart. The lead 14 is shown illustratively as having a defibrillation coil electrode 16 and distal and proximal sense electrodes 18, 20. An external programmer 30 can wirelessly communicate with the canister 12 to provide therapy and sensing instructions to the system and to check various device status, history and diagnostic factors. The present invention is not limited to the specific lead 14 design shown, nor position of either the lead 14 or canister 12, and a variety of details and alternatives are disclosed in the patents and applications cited in the following paragraph, each of which may be used in various embodiments of the present invention.

The example of FIG. 1 shows the lead 14 placed over the ribs, in a subcutaneous position. Other subcutaneous positions may be used, such as described in US PG Pat. Pub. No. 20120029335, and U.S. Pat. Nos. 8,157,813, 7,149,575, 6,721,597, and 6,647,292, the disclosures of which are incorporated herein by reference. In other examples, the lead may be placed beneath the sternum in a substernal position, in the mediastinal space, as described in US PG Pat. Pub. No. 20170021159, and/or U.S. Pat. No. 10,471,267, the disclosure of which are incorporated herein by reference. In still other examples, the internal thoracic vasculature (including the internal thoracic vein or ITV) may be used for implantation as a final placement or as an avenue to the mediastinum, as described in US PG Pub. Nos. 20180133462, 20180036547, 20180036527, the disclosures of which are incorporated herein by reference. Such systems use sensing and therapy electrodes disposed in positions that neither contact nor enter the heart.

Approaches that use pacing electrodes that neither enter nor contact the cardiac tissue call for increased pacing amplitude when compared to transvenous, intracardiac or epicardial electrodes. Historically two separate output paths would be used for an implantable transvenous defibrillator having both pacing and defibrillation therapy capabilities, with a low voltage pacing therapy deliverable directly off of the battery stack or with a limited voltage boost, while a transformer-based circuit would be used to transfer power from the battery to a high voltage (HV) capacitor or capacitor stack for defibrillation purposes. However, with increased pacing amplitude needed for these newer, substernal, ITV, extracardiac or subcutaneous pacing configurations, the prior solutions become less usable. For example, with the SICD System™, three series batteries are used in the device, providing a nominal output voltage in the range of 9 to 9.5 volts, under light load; the pacing output of this system, used in the post-defibrillation shock context, delivers a 200 mA pacing output into a range of impedances from 25 to 200 ohms (assuming impedance measured during shock delivery), which means pacing can be delivered at up to 40 volts, more than four times the battery voltage. Pacing, when delivered, may be used for any of bradycardia support (chronic or post-defibrillation), as an anti-tachyarrhythmia pacing therapy, or for alleviation of heart failure systems, such as resynchronization therapy, without limitation.

Pacing is delivered at a relatively low duty cycle; a higher duty cycle, such as when inducing fibrillation for testing purposes (as is common at implant), can use a higher duty cycle, requiring still more DC:DC boosting capability. Induction testing is performed to demonstrate one or both of the sensing capability of an implanted system and its ability to convert ventricular fibrillation to a normal rhythm with therapeutic shock. In the realm of transvenous defibrillators, there is a trend away from universal induction testing. However, induction testing continues to be widely used, and in particular can be expected to be a continued practice with newer substernal, ITV, extracardiac and/or subcutaneous defibrillation systems.

Some proposals include adding a separate "pacing therapy" boost circuit and capacitor array to provide intermediate level power for pacing purposes. However, provision of multiple, separate circuits to provide the needed boosting increases complexity, cost, and space requirements, as well as complicating other factors such as reliability. A transformer-based circuit can be used to transfer very large amounts of power from a battery to a capacitor stack, and this technology is widely used in implantable defibrillators today to provide higher power cardioversion and/or defibrillation therapy outputs. Moreover, the commonly used output circuit for defibrillation therapy, which is called an H-bridge due to its shape, having first and second high side legs that meet at first and second load nodes with first and second low side legs, is already present in the device. New and better ways to facilitate multiple output levels, without overly complicating the apparatus, are desired.

While the development of the present invention may focus generally on some of the newer implant positions (subcutaneous, substernal, mediastinal or ITV), the present invention may also be used in more therapy systems with still older implantation positions, including epicardial or transvenous systems having leads and/or electrodes located in or on the heart.

Figure 2:
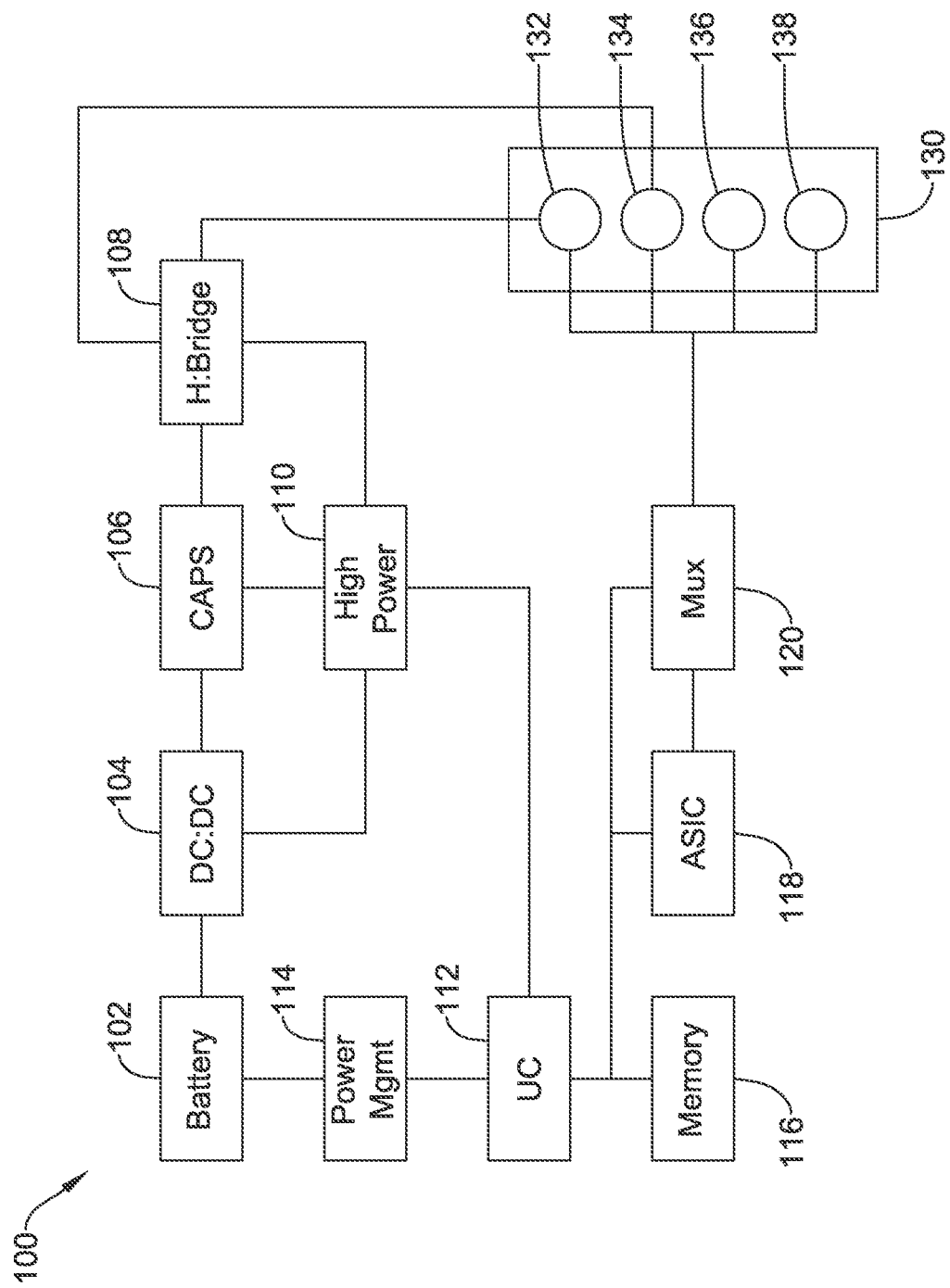
FIG. 2 shows an illustrative block diagram for an implantable stimulus system.

FIG. 2 shows an illustrative block diagram for an implantable stimulus system. The illustrative system 100 is powered by an internal battery 102, which may be of any suitable chemistry for an implantable medical device, such as any of various lithium chemistries (Lithium-Ion, LiMnO2, etc.). The battery 102 may comprise any suitable number of battery cells, such as 1, 2, 3, 4 or more cells. The battery 102 in the example is a non-rechargeable battery; in other examples a rechargeable battery may be used and, if so, a recharging circuit comprising, for example, an inductive coil that can be energized by an external coil may be used, such as described in U.S. Pat. No. 9,814,889 and/or as such systems are known for spinal cord stimulation such as in U.S. Pat. Nos. 8,548,590, 8,473,066 and/or 8,463,392, the disclosure of which are incorporated herein by reference.

The battery 102 can be used for high power therapy delivery by routing the battery output to a DC:DC converter 104 to charge a capacitor stack 106, with an H-Bridge used to issue therapy pulses via electrodes coupled to ports 132, 134. Optionally, in some examples, blocks 104, 106 and 108 reside on a high power hybrid (circuit board) 110 separate from lower power circuitry to reduce interference, among other benefits.

In some examples, a transformer is used as the DC:DC charging circuit, using a flyback transformer layout in which the battery output is directed to a primary coil of the transformer and one or more secondary coils each charge a capacitor of the capacitor stack 106. In operation, the charging sequence alternates between primary and secondary phases. During the primary phase, the transformer receives power from the battery 102, with current passing from the battery, through at least a switch and the transformer to ground. During the secondary phase, the switch is opened, causing an open circuit of the transformer primary coil, driving the energy stored in the transformer during the primary phase into the capacitor stack 106. Appropriately placed diodes can be used to manage current flow and ensure appropriate charging takes place. Switching between primary and secondary phases can be controlled via a timing schedule, or may occur in response to measured currents reaching upper or lower thresholds, or a combination of both, such as having a fixed interval primary phase and a current controlled secondary phase.

While several references herein are to a capacitor stack 106, having, for example, anywhere from 2-6 capacitors, or more, a single capacitor may be used if desired. The drawing indicates dedicated output or output ports 132, 134 which may be, for example, an output coupled to a conductive canister (or portion thereof) that contains the circuitry 100 and an electrode on a lead. In other examples, two lead electrodes, or two housing electrodes, or more than two electrodes may be used for therapy delivery; additional switching circuitry may be used to direct therapy outputs as desired.

In the illustrative example, lower power circuitry is (optionally) powered by a power management block 114 that provides regulated voltages off of the battery 102, such as, for example and without limitation, 1.8, 3.2, 5.1, or other voltages, which are typically reduced relative to the battery output to ensure stable voltages over the useful life of the device, during which the battery voltage typically degrades. Some examples may also include, for example, a 15 volt supply that can be generated by a switched capacitor voltage booster (assuming the battery 102 provides less than 15 volts). A plurality of such power supplies may be included to address various needs in the system, such as, for example and without limitation, providing a 5-volt supply to power a telemetry antenna while a 3.2 volt supply powers a microcontroller.

A microcontroller 112 may be provided for managing various device operations, with a memory 116 provided to store executable instructions as well as device history data, such as measured battery voltages and recorded cardiac data related to "episodes" in which therapy is delivered, as well as any other information or instructions used in the system. An application specific integrated circuit (ASIC) 118 is illustratively shown and, without intending to limit the invention any particular one of these items, may include circuits dedicated to particular tasks, such as an input ECG circuit that filters, amplifies and digitizes sensed signals. Other circuits on the ASIC may include dedicated beat detection circuitry, and/or dedicated morphology analysis circuitry such as a correlation analysis or wavelet comparison circuit. The ASIC 118 may comprise or be coupled to telemetry circuitry using, for example, Medradio, inductive telemetry, or Bluetooth (including Bluetooth Low Energy) communication circuitry. The power management block 114, or portions thereof, may be integrated into the ASIC 118 if desired.

A switching circuit is also shown as a multiplexor 120 for coupling to a plurality of inputs/outputs 130, shown as four input/output lines 132, 134, 136, 138; more or fewer input/output lines may be included. In some examples the switching circuitry is used to select one or more sensing vectors defined by pairs or groups of electrodes used for sensing purposes, such as disclosed, for example, in U.S. Pat. Nos. 8,825,157, 7,783,340, 8,200,341, and/or US PG Pat. Pub. Nos., 20170113053, 20170113050, 20170113040, and/or 20170112399, the disclosures of which are incorporated herein by reference.

Figure 3:
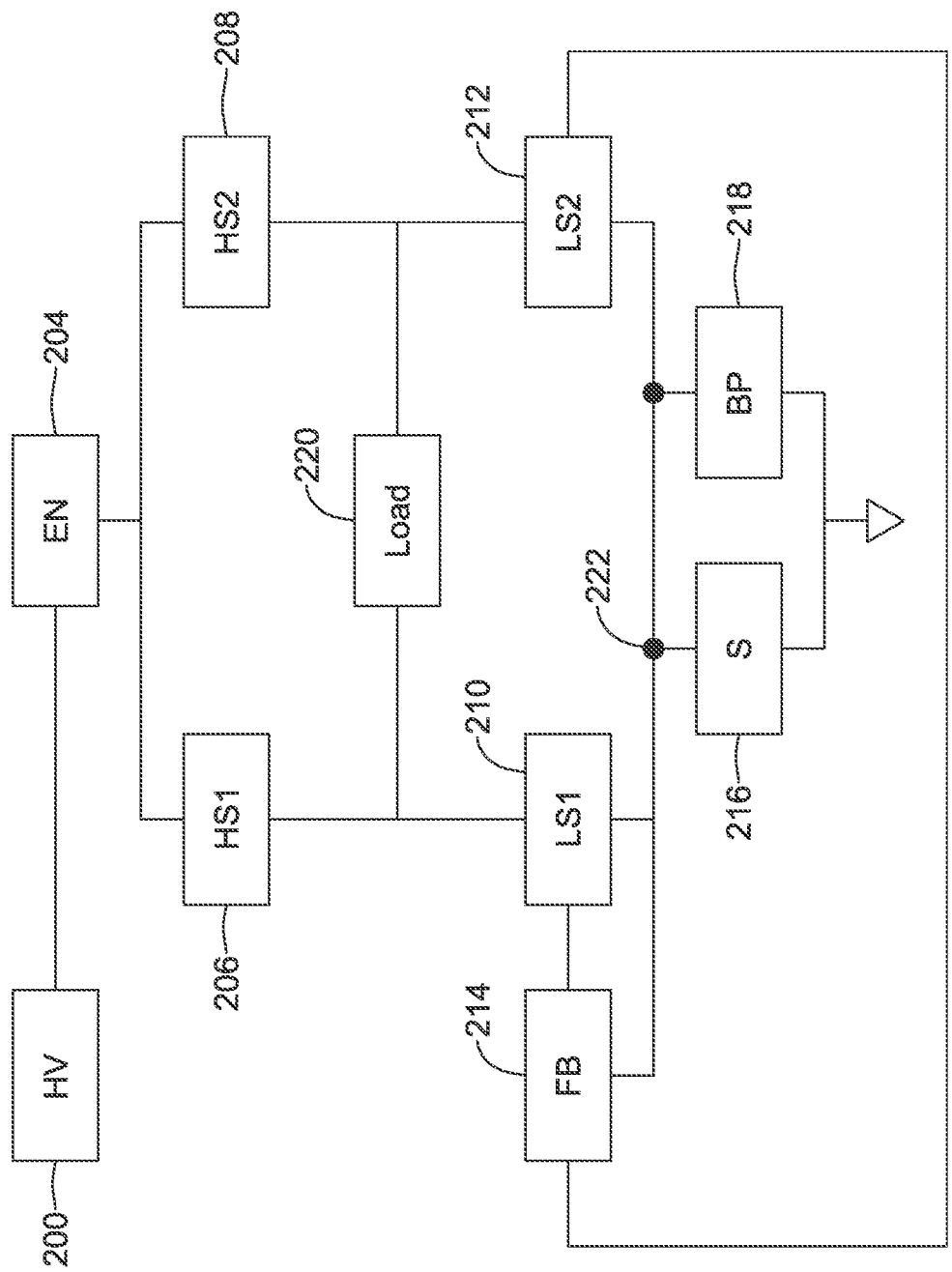
FIG. 3 shows a prior art output circuit.

FIG. 3 shows a prior art output circuit. The illustrative circuit delivers power from the HV Capacitors 200 to a load 220, which represents the patient. An enable switch 204 sit outside (above) the H-Bridge, which comprises two high side switches 206, 208 and two low side switches 210, 212. In this example, the low side switches 210, 212 can be used as ON/OFF switches during defibrillation, and can be used to control current during pacing and induction processes by the use of a feedback circuit 214. Between the H-Bridge and ground are a sense resistor 216 and a bypass switch 218.

To issue therapy, a combination of the enabling switch 204 and one high side and one low side switch are closed. In a first polarity output, switches 204, 206 and 212 are closed; to deliver output of the opposite polarity, switches 204, 208 and 210 are closed. During defibrillation therapy, the sense resistor 216 is bypassed by closing the bypass switch 218, and current flow is determined by the voltage from the HV capacitors divided by the impedance of the load 220 and any line impedance/parasitics, which are generally small relative to the load 220. Biphasic therapy can be issued by monitoring the HV capacitors 200 to determine when a threshold voltage for switching polarity is reached, such as 40, 50, 60, or 70% (or other value) drop in voltage.

For controlled current pacing and induction purposes, the bypass switch 218 is opened, forcing current through the sense resistor 216. The feedback circuit 214 obtains a sense signal from the sensing node 222 and provides a controlled enabling voltage to one of the low side switches 210, 212 (depending on which polarity of output is active) to keep the voltage at node 222 fixed to a predetermined value. For example, when the voltage at node 222 is lower than a target value, that means less than a target current is flowing through sense resistor 216, so the voltage provided to enable whichever of switches 210, 212 is being operated is increased until the voltage at node 222 reaches the target value.

To limit the amount of power that has to be absorbed by switches 210, 212, the HV capacitors 200 are charged for pacing and induction to a voltage that is lower than that used for defibrillation, as, for example, by charging to a level that will enable current to reach the target value for the maximum allowable load impedance. For example, if the maximum allowable, or expected, load is 200 ohms and the current to be issued is 200 mA, then the HV capacitors 200 may be charged to a value that exceeds 40 volts plus some margin to account for losses due to the transistors and transmission lines in the circuit, as well as attenuation in the sense resistor 216, for example resulting in a voltage in the range of 45 to 100 volts, rather than several hundred or thousand-plus volts used for defibrillation.

A drain circuit for the HV capacitors 200 is omitted in the drawing, but may be understood as comprising one or two resistive branches. In a two-branch version, a passive drain branch having a large impedance (1 Mohm, for example) provides a slow drain on the HV capacitors to ensure that a large voltage is not held indefinitely, while a smaller resistor, sometimes called a dump resistor (10 kohm, for example), is provided in series with a switch to allow the HV capacitors 200 to be quickly drained to a reduced voltage if needed, for example, to allow pacing therapy output after a defibrillation shock if reduced HV cap voltage is desired during pacing relative to the residual voltage after defibrillation shock. Another context for using an active drain branch may be if a patient undergoing induction testing spontaneously converts to normal rhythm while the HV capacitors 200 are being charged, in which case is may be desirable to drain the HV capacitors 200 prior to the next induction attempt.

In this circuit, because the low side switches 210, 212 are used to control current flow, they have to absorb a significant amount of power in the controlled current mode, and typically relatively large IGBT devices are used. Also in this circuit, the high side switches 206, 208, and the enable switch 204, are subject to a level shift during therapy output, as the load raises the emitter voltage on each to, practically speaking, the voltage on the HV capacitors 200. Therefore an isolation circuit element, such as a transformer or optical isolator, is typically used to provide the control signal to each switch 204, 206, 208, reliant on a low voltage input. The use of larger IGBT elements and the isolation elements increases cost and size of the circuit, and the isolation circuits may also add to the potential for quality issues, as optical isolators can be subject to thermal issues during manufacturing. Alternatives are desired.

Figure 4:
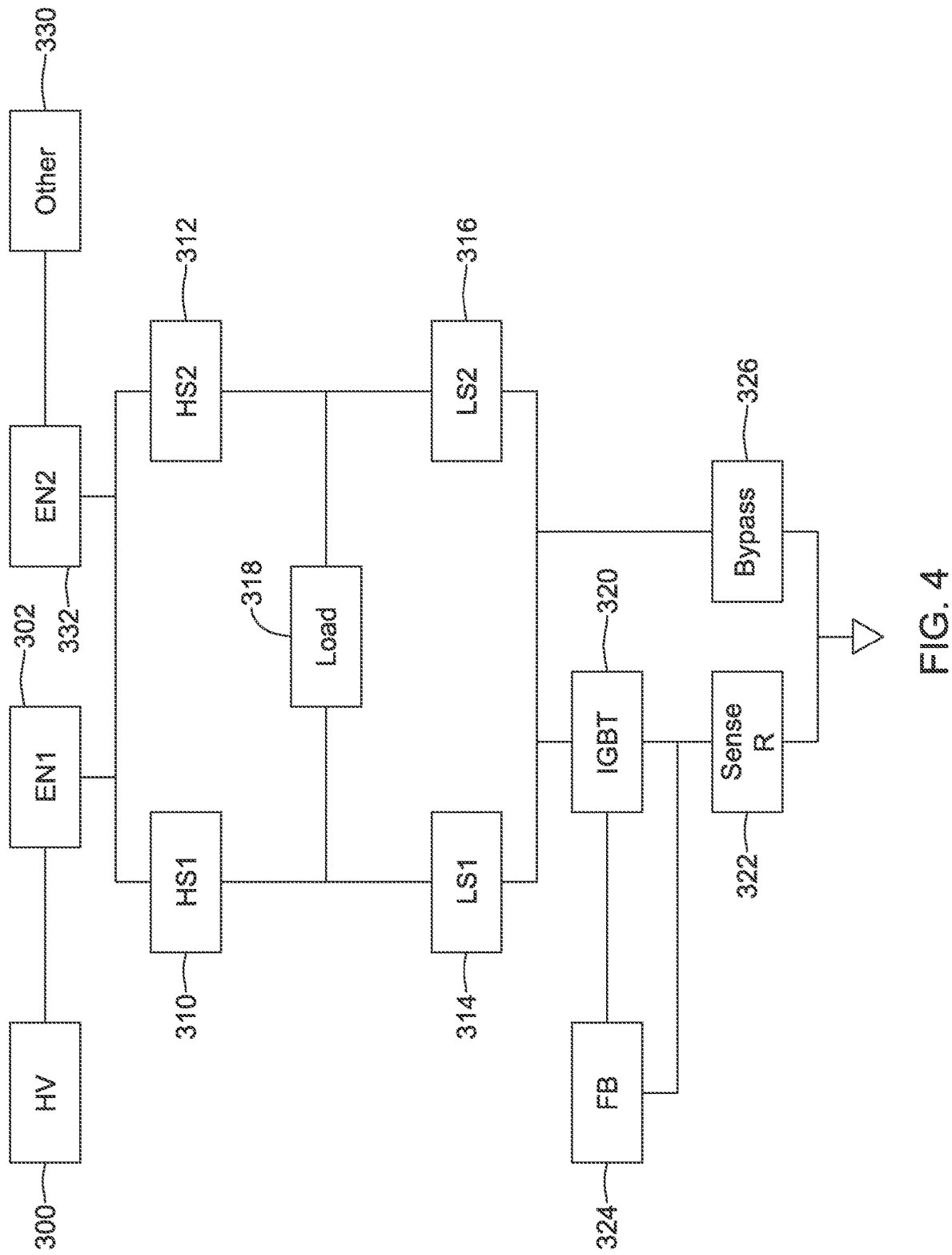
FIGS. 4-5 show new output circuit designs in block form.
Figure 5:
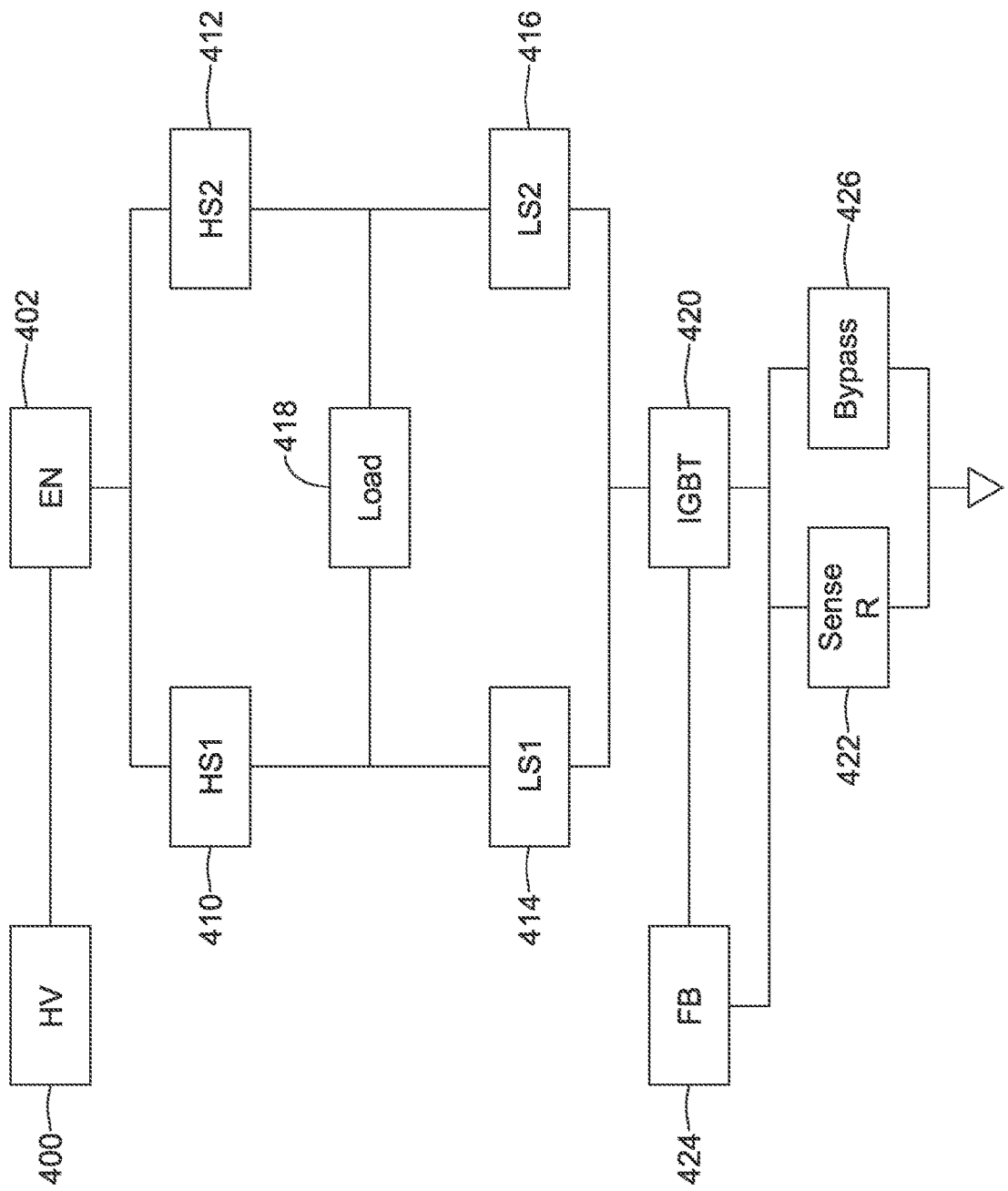

FIGS. 4-5 show new output circuit designs in block form. Starting with FIG. 4, a first therapy output circuit is shown as an HV circuit 300. For example, the HV circuit 300 may include a capacitor or set of capacitors and associated protection, filtering or other circuitry (such as diodes that ensure current only flows in a desired direction), where the HV circuit 300 may be coupled to further circuitry, such as a charger or battery, to provide energy thereon. The HV circuit 300 may, in some examples, take the form of a transformer or resonant circuit that provides a therapy output circuit. While an HV circuit 300 is represented in FIG. 4, it is not necessary for the first therapy output circuit to be a high voltage circuit as that term may be used in, for example, a defibrillator (where "high voltage" may mean a voltage over 100, 400, 800, or 1000 volts); in other examples the first therapy output circuit may be a regulated voltage from a battery power supply, or may be a current or voltage coming from an energy receiving circuit such an inductive coil that receives power wirelessly or remotely from a second device.

The HV circuit 300 is coupled to an H-bridge, optionally, by a first enable switch 302. The H-bridge is illustrated in this example as including first and second high side switches HS1 310 and HS2 312, and first and second low side switches LS1 314 and LS2 316, providing output in a selectable polarity to a load 318. The load 318 may be, for example, a patient tissue volume to which electrical signals are directed via one or more contacts that are in turn coupled to a lead in a device header or lead port, where the lead may be permanent or removeable. The load 318 may also be coupled to via an active canister electrode, that is, a conductive housing or portion thereof for the device circuitry.

A current controlling circuit is coupled between the H-bridge and ground by electrical coupling to the first and second low side switches LS1 314 and LS2 316. In this example, the current controlling circuit comprises a current controlling switch 320 that routes current to a sense resistor 322, with a feedback circuit 324 taking a feedback signal from the high side of the sense resistor 322. In this configuration, the feedback circuit 324 thereby receives a signal indicative of the voltage drop across the sense resistor 322. In operation, the feedback circuit 324 can monitor the voltage cross the resistor 322, which is proportional to the current, and provide a driving signal to the current controlling switch 320 to increase, decrease, or maintain the current passing therethrough. In this example, the current controlling switch 320 is shown as an insulated gate bipolar transistor (IGBT). In other examples, a MOSFET, such as a power MOSFET or high voltage MOSFET may be used instead (wherein high voltage in this context may mean capable of handling at least 100 volts of source to drain voltage), or in still other examples, a bipolar junction transistor (BJT) may be used instead.

The circuit is also shown as having, optionally, a second output circuit 330, coupled to the H-Bridge by a second enable switch 322. The second output circuit 330 may be a therapy circuit providing a different power/amplitude capability than the first therapy output circuit, or may provide different waveform characteristics such as by providing a sinusoidal output signal, if desired. The second output circuit 330 may be a second therapy output, or may be non-therapeutic. For example, a non-therapeutic output may be provided to perform communication by conducted communication, as described in U.S. Pat. Nos. 10,213,610, 10,050,700, the disclosures of which are incorporated herein by reference, and circuitry for generating such outputs may be coupled via the H-bridge to tissue, if desired. In some examples, the second output circuit 330 may be a subset of the components of the first output circuit 300, as described in U.S. Provisional Patent App. No. 62/976,141, filed Feb. 13, 2020, titled OUTPUT CIRCUITRY FOR MULTIPLE-THERAPY IMPLANTABLE DEVICES, the disclosure of which is incorporated herein by reference.

In the circuit shown, several switches can be implemented as latching switches, such as a silicon controlled rectifier (SCR), an anode gate thyristor (AGT), a triode for alternating current (TRIAC), etc. Latching switches, once enabled, can latch into a closed operating mode until the current passing therethrough drops below a threshold, at which point the latching switch de-latches and ceases to pass current. For example, EN1 302 and the H-bridge switches 310, 312, 314, 316 may all be latching switches, while the current controlling switch 320 is not a latching switch and instead passes current therethrough in a mode that responds, in terms of the amount of current that can pass, in response to an enabling signal. For example, an IGBT or MOSFET can be used to control current passing therethrough by managing the gate-emitter voltage. A BJT can be used to control current passing therethrough by controlling the base-emitter voltage.

The circuit is shown as also having, optionally, a bypass switch at 326, which can be used when a non-current-controlled output is desired to bypass the current controlling circuit 320, 322, 324. If the bypass switch 326 is included, it may also be a latching switch, or it may not be a latching switch, depending on other features in the system and desired operation. For example, in a defibrillation output circuit, it can be desirable to truncate one or more phases of the output therapy; if so, a non-latching switch would be needed somewhere in the output circuit path when the bypass switch is used to deliver the non-current-controlled defibrillation therapy (assuming a non-current controlled defibrillation therapy is desired). To provide the truncation function, the bypass switch 326 may be a non-latching configuration such as by using a MOSFET (or other non-latching field effect transistor), IGBT and/or BJT. In other examples, an enable switch 302 may be a non-latching switch to allow for truncation of the output when desired.

With the configuration shown, one advantage may be that the current controlling switch (as shown, IGBT 320, though as noted other examples may use a MOSFET or BJT if desired) would not have to accommodate high currents associated with defibrillation, easing the design constraints on that particular component. For example, while induction or pacing outputs may be in the range of one to several hundred milliamps, a defibrillation pulse may generate a peak current of several amperes of output current (as, for example, when an S-ICD System issues an output of 1350 volts into a patient impedance of 100 ohms or less).

FIG. 5 shows another example. Here, a therapy output, shown as HV block 400 (which may have designs and features as described above for block 300 in FIG. 4), is coupled by an optional enabling switch 402 to an H-Bridge having high side switches HS1 410 and HS2 412 and low side switches LS1 414 and LS2 416, for coupling to a load 418. The enable and H-bridge switches 402, 410, 412, 414, 416 may be as described above for corresponding blocks in FIG. 3.

The output of the H-bridge is routed to a current controlling circuit having a current controlling switch 420 which provides an output having two paths to ground. A sense resistor 422 provides a first path to ground, and a bypass switch 426 provides a second path to ground. Again, the current controlling switch 420 is illustrated as an IGBT but may take other forms, such as a high voltage or high power MOSFET or a BJT, if desired. A feedback circuit 424 takes a signal from the high side of the sense resistor 422, where the signal is indicative of the voltage drop across the sense resistor 422, and provides a driving or enabling signal to the current controlling switch 420.

When a current controlled output is desired, the bypass switch 426 is disabled and does not conduct current, passing the output current of the H-bridge and current controlling switch 420 through the sense resistor 422, providing a usable signal to the feedback circuit 424. If a non-current controlled output is desired, the bypass switch 426 can be closed, shorting the sense resistor 422. The feedback circuit 424 will thus sense no current passing through the sense resistor 422 and provides a maximum signal to the current controlling switch 420, such that the current controlling switch 420 does not attenuate current, and an uncontrolled current output is provided. To truncate the output current, the current controlling switch 420 may be opened, or both of the bypass switch 426 and the current controlling switch 420 may be opened.

As can be seen, the location of the bypass switch 426 is different in FIG. 5 than in FIG. 4, but other aspects of the circuit are generally the same. The bypass switch 426 may, or may not, be a latching switch, since the current controlling switch 420 can be used to truncate therapy output. Because both the controlled current and non-controlled currents pass through the current controlling switch 420, the current controlling switch 420 may be required to handle larger currents with the layout of FIG. 5 than it would with FIG. 4, which may increase component cost in some examples.

Referring now to each of FIGS. 4 and 5, the bypass switch or block shown at each of 326 and 426 may omit a switching apparatus in some examples, and instead can use a diode or rectifier-based configuration to allow higher current/voltage to bypass the sense circuitry at 322 and/or 422. A forward biased diode/rectifier, or reverse biased Zener diode, may be used in place of a switch in either 326 or 426, as long as the current sensing blocks 322/422 (and in FIG. 4, the IGBT 320) have sufficient current carrying capacity to accommodate however much current would flow during defibrillation due to the forward voltage of the diode/rectifier (or reverse breakdown voltage if a Zener diode is used). Thus, for example, if the feedback is configured to sense a voltage of 3 volts or less, a diode having a forward voltage greater than 3 volts (or two or more diodes in series) may be used instead of a bypass switch at 326 and/or 426, simplifying the control setup. In an example, the feedback circuits 324 and 424 may include an analog-to-digital convertor having a dynamic range that is less than the bias of the one or more diodes used in the bypass circuit 326, 426. When selecting specific components, particularly for the layout in FIG. 5, is may be necessary to consider latency within the circuit to ensure, for example, that when truncating an output, the voltage across the bypass path cannot rise fast enough to turn on a diode before latching elements elsewhere in the circuit can turn off, as this may impair the ability to truncate pacing or defibrillation pulse phases. If a diode configuration is used in the layout of FIG. 5, it may be desirable in some implementations to include a non-latching switch as the enable switch above the H-Bridge, that is, between the H-Bridge and the relevant output signal source such as the HV capacitor(s), or, in the alternative, to use non-latching switches in at least one of the upper or lower legs of the H-Bridge, to ensure that turn-off can be controlled.

In still other examples, the feedback circuit 324, 424 may be configured to sense the feedback signal when the system is using a current controlled output mode, and to generate a current controlling signal therefrom. Such as signal may be compared to a threshold to determine if the current is above or below a target, or, in the alternative, may itself indicate whether the current is above or below a target that the feedback circuit itself analyzes. In such examples, to perform a non-current controlled output, the system may either not sense (by disabling or powering down an ADC or amplifier, for example or to sense but generally ignore the current controlling signal from the feedback circuit when performing, for example and without limitation, a voltage controlled defibrillation therapy.

Figure 6:
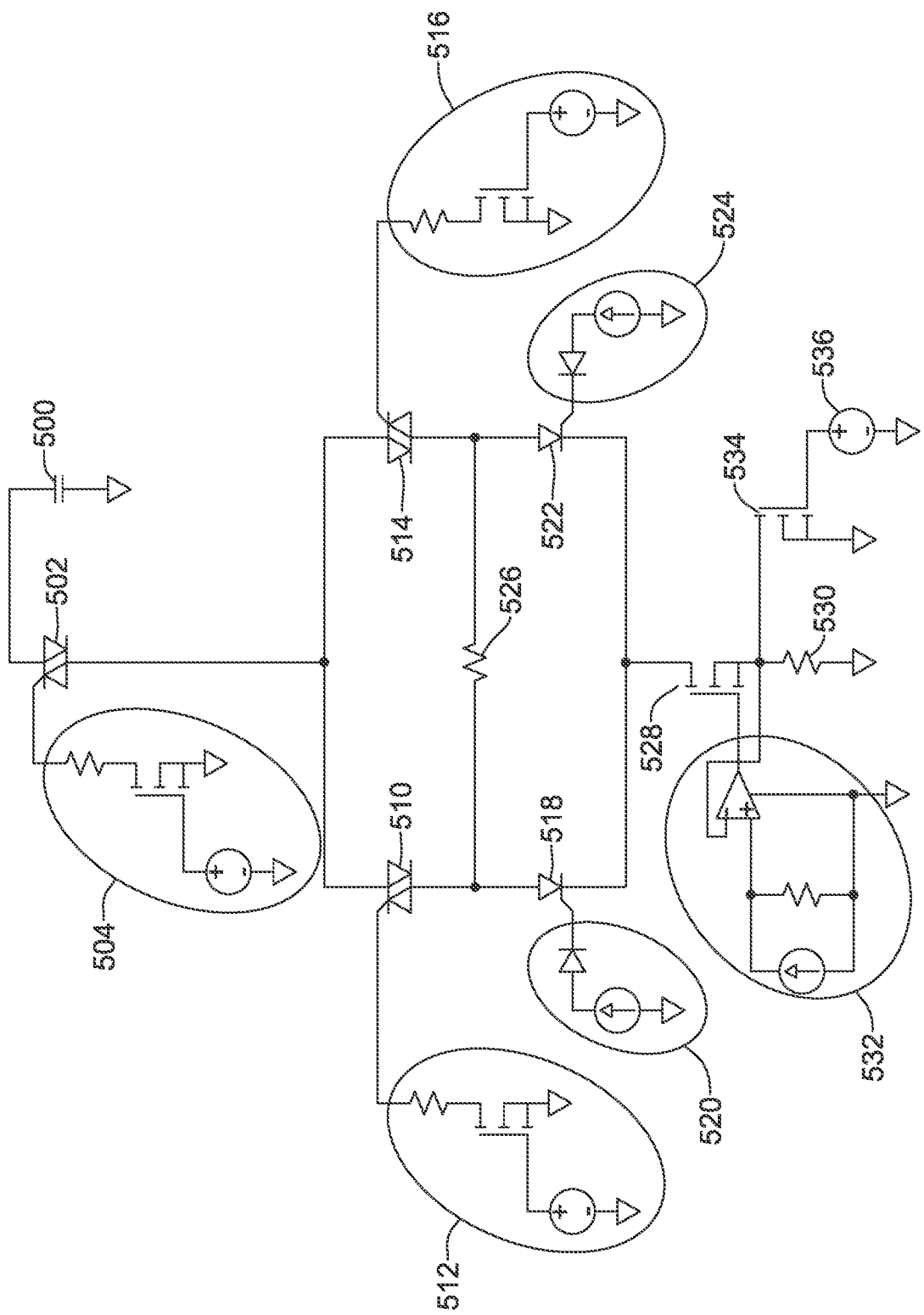
FIG. 6 shows another new output circuit design in schematic form.

FIG. 6 shows another new output circuit design in schematic form. Here, a therapy output source is shown as a capacitor 500 (which may couple to a charging circuit that is not shown), which is coupled by an enable switch 502 to an H-bridge circuit. The enable switch 502 is shown as an AGT, but may be a SCR, TRIAC, or other thyristor design or latching circuit, or may be a non-latching circuit element such as an IGBT, BJT or MOSFET, if desired. A driving circuit is shown at 504 for the enable switch 502; the driving circuit 504 is specific to an AGT or TRIAC device, but other driving circuits may be used to accommodate other switches, whether latching or not.

The H-bridge is shown having high side switches 510, 514, and low side switches 518, 522, to control output delivery and polarity to a load 526. Driver circuits are shown for each H-bridge switch at 512, 516, 520, 524, with each driver specific to a particular switch type in the H-bridge. As shown, the high side switches 510, 514 may be AGT or TRIAC devices, with appropriate drivers 512, 516 for each, though other switch designs and types, with suitable drivers, may be used in other examples. The low side switches are shown as SCR devices, with appropriate drivers 520, 524. In the example, it may be noted that the low side switches 518, 522, as SCRs, provide additional control over the direction of current flow. While such a configuration may be advisable, it is not required. While FIG. 6 (and other Figures herein) show only two legs in each of high and low sides of the H-Bridge, more legs may be provided if desired.

Between the H-bridge and ground is a specific implementation, shown for illustration and not to be understood as limiting the invention, of a current controlling circuit with built-in bypass. Here, a field effect transistor, such as a MOSFET (preferably a high voltage and/or high power MOSFET) is used as a current controlling switch at 528, with a sense resistor 530 provided in parallel with a bypass switch 534 that is also shown as a field effect transistor such as a MOSFET. A feedback circuit is shown at 532, in this example, using a current source passing current to a resistor that provides an input to the non-inverting input of a comparator or operational amplifier, which provides a driving signal to the current controlling switch 528. The current source as shown may be implemented using a current mirror, if desired, or may be replaced with a digital-to-analog convertor, if desired, to allow the current used in a controlled current mode to be increased or decreased to suit the application and patient. For example, different patients may have different pace-capture thresholds, depending on, for example, anatomy and placement of the electrodes of the implantable pulse generator/lead, and so a variable current may be used to provide a pacing signal that meets the pace capture threshold without using excess current. Other examples may have a fixed current output.

Throughout the above description, the feedback circuitry is described generally as taking a measurement of current and adjusting a control signal provided to a current controlling device. It should be readily understood that each of proportional, integral and differential control may be integrated in this control approach.

The selection of switch types and driver circuits shown in FIG. 6 is intended to be illustrative, and may be changed in accordance with the remarks above described alternatives for the implementation thereof.

For the above examples, one design feature to be considered is how long any enable signal is to be provided to any latching circuit. In some examples, it may be useful to provide such an enable circuit for a relatively long period (one or more milliseconds, for example) to ensure complete turn-on of all switches in a particular output path as current begins to flow.

Therapy decision making may include any of a variety of algorithms known in the art. In general, referring back to FIG. 1, the microcontroller 112 and associated memory and ASIC components may be adapted to receive electrical signals from the electrodes which are amplified and filtered to provide an input ECG signal. The input ECG signal can be compared to a time-varying threshold to detect heart beats, such as by detecting R-waves or QRS complexes in the cardiac signal. Such detections can be confirmed by analyzing for double detection and noise using known methods. The time elapsing between detected heart beats is recorded in order to calculate cardiac rate, which can be categorized suitable for a given system. For example, a pacemaker defibrillator may have a timeout period applied to detect long pauses between beats, indicating pacing should be delivered for bradycardia conditions. An adaptive pacemaker may use an input from, for example, a temperature sensor or motion detector, to adjust the timeout period to account for patient activity, allowing the paced heart rate to increase or decrease depending on patient activity. A defibrillator or tachyarrhythmia therapy system may also classify ventricular tachyarrhythmia (VT) and ventricular fibrillation (VF) rates, such as considering rates between 180 and 220 beats per minute (BPM) as VT, and rates above 220 BPM as VF (other rate threshold may be used, and the thresholds may be configurable by a physician or at a physician's request/order). VT rates may be used to trigger ATP, for systems that provide ATP and in which ATP is enabled. VF rates may trigger additional analysis for shock delivery, such as using an X/Y counter to determine how many beats (X) of a set of Y beats are deemed to indicate VF using, for example, shape analysis (morphology). Illustrative shape analysis techniques can include the use of correlation waveform analysis, in which a stored template of a "normal" beat electrical signature is compared to detected beats; low correlation may be deemed indicative of VF; detected beats may be compared one to another as well to differentiate VT from VF and/or to differentiate sinus tachycardia (resulting from exercise, for example) from VT and VF. Wavelet transformation analysis may also be used to analyze shape, as well as the width of beats. When VF is identified, preparations for defibrillation therapy can be commenced, including charging the capacitor stack to a defibrillation energy level (typically 30 Joules or more, and higher still if a subcutaneous-only system is used, where 60 Joules or more may be used).

In an example, a beat detection routine may be as described in U.S. Pat. No. 8,565,878, with cardiac signal analysis for overdetection performed as in U.S. Pat. No. 8,160,686. Arrhythmia discrimination may be performed using methods described in U.S. Pat. Nos. 6,754,528 and/or 7,330,757. With beats analyzed for arrhythmia, the overall rhythm may be assessed using methods as in US Patent Application Pub. No. 2006/01467503, and defibrillation therapy can be delivered when all requirements for defibrillation therapy have been met, meaning that sufficient arrhythmic beats are detected in a persistent manner allowing positive confirmation of treatable arrhythmia. The disclosures of each of these patents and patent applications are incorporated herein by reference for at least the purposes identified for each. However, other methods may be used at each step, if desired, and the invention is not limited to use with these particular algorithms.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An electronic circuit for controlling an output of an implantable medical device, the electronic circuit comprising:
an H-bridge comprising first and second high side legs having first and second high side switches, and first and second low side legs having first and second low side switches, defining first and second nodes for outputting a therapy signal from the implantable medical device;
a first therapy output circuit coupled to the H-bridge; and
a current controlling circuit coupled between the low side legs of the H-bridge and ground;
wherein the current controlling circuit comprises a current controlling switch coupled in series to a sense resistor, and a feedback circuit configured to receive a signal indicating a voltage drop across the sense resistor and generate a control signal to the current controlling switch.

2. The electronic circuit of claim 1 wherein each of the first and second low side switches are latching devices.

3. The electronic circuit of claim 1 wherein each of the first and second high side switches are latching devices.

4. The electronic circuit of claim 1 wherein the coupling of the therapy output circuit to the H-bridge includes a first enable switch, the first enable switch being a latching device.

5. The electronic circuit of claim 1 further comprising a second therapy output circuit coupled by a second enable switch to the H-bridge, the second enable switch being a latching device.

6. The electronic circuit of claim 1 wherein the current controlling switch takes the form of an IGBT.

7. The electronic circuit of claim 1 wherein the current controlling switch takes the form of a high voltage MOSFET.

8. The electronic circuit of claim 1 wherein the current controlling switch takes the form of a high voltage bipolar junction transistor.

9. The electronic circuit of claim 1 further comprising a bypass path parallel to the current controlling circuit and configured to allow current to bypass the current controlling circuit.

10. The electronic circuit of claim 1 further comprising a bypass path parallel to the sense resistor and configured to allow a current from the current controlling circuit to bypass the sense resistor.

11. The electronic circuit of claim 10 wherein the bypass path comprises a diode.

12. The electronic circuit of claim 10 wherein the bypass path comprises a switch to selectively allow current to pass therethrough.

13. An implantable defibrillator comprising a housing and operational circuitry therein, the operational circuitry comprising:
at least one battery;
at least one high power capacitor;
a transformer configured to selectively transfer energy from the battery to the high power capacitor;
a system controller configured to control operation of the transformer; and
an output control circuit coupled at least to the at least one high power capacitor, such that the at least one high power capacitor serves as a first therapy output circuit, and comprising:
an H-bridge comprising first and second high side legs having first and second high side switches, and first and second low side legs having first and second low side switches, defining first and second nodes for outputting a therapy signal from the implantable medical device; and
a current controlling circuit coupled between the low side legs of the H-bridge and ground;
wherein the current controlling circuit comprises a current controlling switch coupled in series to a sense resistor, and a feedback circuit configured to receive a signal indicating a voltage drop across the sense resistor and generate a control signal to the current controlling switch.

14. The implantable defibrillator of claim 13 wherein:
the coupling of the first therapy output circuit to the H-bridge includes a first enable switch, the first enable switch being a latching device;
each of the first and second low side switches, and each of the first and second high side switches, are latching switches;
the current controlling circuit comprises a current controlling switch coupled in series to a sense resistor, and a feedback circuit configured to receive a signal indicating a voltage drop across the sense resistor and generate a control signal to the current controlling switch; and
the current controlling switch is a non-latching switch enabling truncation of an output constant current signal.

15. The implantable defibrillator of claim 13 wherein the current controlling switch takes the form of an IGBT.

16. The implantable defibrillator of claim 13 further comprising a bypass path parallel to the sense resistor and configured to allow a current from the current controlling circuit to bypass the sense resistor.

17. The implantable defibrillator of claim 16 wherein the bypass path comprises a diode.

* * * * *